United States Patent [19]

Richardson et al.

[11] Patent Number: 5,217,995
[45] Date of Patent: * Jun. 8, 1993

[54] PESTICIDAL COMPOSITIONS

[75] Inventors: Barry A. Richardson, Winchester; Timothy R. G. Cox, Bishops Waltham; Stuart W. Carter, Berkhamsted, all of England

[73] Assignee: Burroughs Wellcome Co., Research Triangle Park, N.C.

[ * ] Notice: The portion of the term of this patent subsequent to Sep. 10, 2008 has been disclaimed.

[21] Appl. No.: 654,242

[22] Filed: Feb. 12, 1991

Related U.S. Application Data

[63] Continuation of Ser. No. 406,191, Sep. 12, 1989, Pat. No. 5,047,423, which is a continuation of Ser. No. 654,315, Sep. 25, 1984, abandoned.

[30] Foreign Application Priority Data

Sep. 29, 1983 [GB] United Kingdom ............... 8326173
May 31, 1984 [GB] United Kingdom ............... 8413916

[51] Int. Cl.$^5$ ................... A01N 37/34; A01N 53/00; C09D 5/14
[52] U.S. Cl. ................. 514/521; 514/531; 514/731; 514/919; 106/15.05; 424/DIG. 10
[58] Field of Search ............ 106/15.05; 514/521, 514/531, 731, 919; 424/DIG. 10

[56] References Cited

U.S. PATENT DOCUMENTS 3,930,025 12/1975 Albright et al. ............... 514/731

FOREIGN PATENT DOCUMENTS 2038636A 7/1980 United Kingdom .

OTHER PUBLICATIONS

Baker, et al., Synthetic Pyrethroid Insecticides as Replacements for Chlorinated Hydrocarbons for the Control of Wood-Boring Insects, pp. 121–127, (1980).
The Merck Index, 1976, p. 2573.
Y. Inoue, Termiticidal Activities of Synthetic Pyrethroids, vol. 1, pp. 113–118.
Report, Penarth Research Centre, Review of Recent Developments and Trends in Wood Preservation, (Jan. 1978 to Jun. 1980), Aug., 1980, 14 pages.
Paper, p. 157, vol. 99, 1983, 5-Agre chemicals.
Paper, Sumitomo Chemical KK, Nov. 26, 1975, 49620Y/28.

*Primary Examiner*—John W. Rollins
*Attorney, Agent, or Firm*—Donald Brown; George W. Neuner

[57] ABSTRACT

Compositions for treating timber, especially timber to be exposed to the ground, comprising creosote and a compound of formula I:

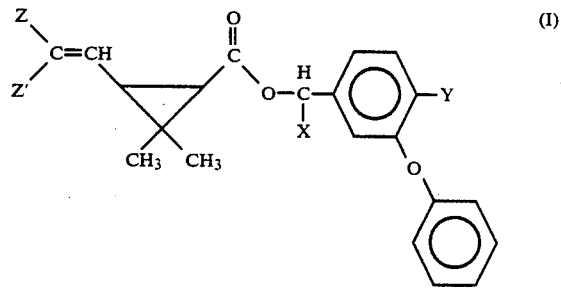

wherein Z and $Z^1$ are the same or different and are each halo, halophenyl or haloalkyl, X is hydrogen or cyano, and Y is hydrogen or a fluorine atom.

The preferred pyrethroid is Permethrin.

The compositions are unusually stable and have a prolonged protective action against termites, beetles, molluscs, woodworm and the like.

7 Claims, No Drawings

PESTICIDAL COMPOSITIONS

This is a continuation of copending application Ser. No. 07/406,191 filed on Sep. 12, 1989, now U.S. Pat. No. 5,047,423, which is a continuation of U.S. Ser. No. 06/654,315, filed Sep. 25, 1984, now abandoned.

BACKGROUND OF THE INVENTION

This invention relates to compositions for the preservation of timber.

It is known to use pesticides of the pyrethroid class to protect timber from attack by insects and other pests (see Japanese Patent Application No. 52-66603; 1975; Sumitomo). However, pyrethroids are relatively expensive pesticides and this can be disadvantageous when a high volume, low cost material such as wood is being treated. Furthermore, pyrethroids are known to be short-lived when exposed to soil. The most commonly used timber-protecting pesticides are, in many cases, thus still relatively toxic but cheap compounds such as lindane (gamma-hexachlorocyclohexane).

It has also been known for many years to use creosote to protect timber. Creosote has the advantage of being cheap, but wood treatment with creosote is unpleasant to handle, being oily and smelly. In addition, the creosote has to be applied to the timber in such quantities that it may later bleed out of the timber again and cause a fire hazard. One solution which has been adopted is to pretreat the timber with CCA (a mixture of copper, chromium and arsenic compounds) before treatment with creosote. However, CCA is fairly toxic, and a two-stage treatment process adds to the cost of the treated timber. It is not possible to mix CCA with creosote to give a single step process, as the mixture is not stable. Indeed, the problem of instability is encountered with many such mixtures. UK Patent Application No. 2 038 636 (Sumitomo) disclose the use of the insecticides fenvalerate and fenpropathrin to protect timber. It is stated that these compounds may be combined with a fungicide to obtain additionally a fungicidal effect, and creosote is mentioned, in a long list of other fungicides, as being suitable for this purpose. It has now been found that many of these fungicides are unsuitable, as the insecticide is degraded. It is stated in the Sumitomo specification that "when contact between wood and soil is unavoidable . . . an aqueous dilute solution containing the present composition . . . may be mixed with or injected into soil around the wood . . . "

It has now suprisingly been found that mixtures of certain halogenated pyrethroid insecticides and creosote are relatively stable and have a relatively prolonged protective action even when the timber is exposed to soil, without any need to treat the soil as well.

In a report dated August 1980 and sent to a limited number of organisations, the Penarth Research Centre (of Winchester, Hants, UK) stated that "tar oil and organic solvent preservatives intended to give protection against marine borers should always contain organochlorine insecticides to give improved protection against Crustacean borers such as Gribble. It has now been shown that pyrethroids have similar advantages. Whilst these insecticides are expensive, low retentions can achieve much more efficient control than even exceptionally high retentions of normal fungicidal preservative components". There was no suggestion that timber for burial in the soil could also be treated advantageously in the manner, and it was not stated or shown that pyrethroids would be stable in tar oils or the like.

BRIEF SUMMARY OF THE INVENTION

One aspect of the present invention provides a composition for the treatment of timber, the composition comprising creosote and a compound of formula (I):

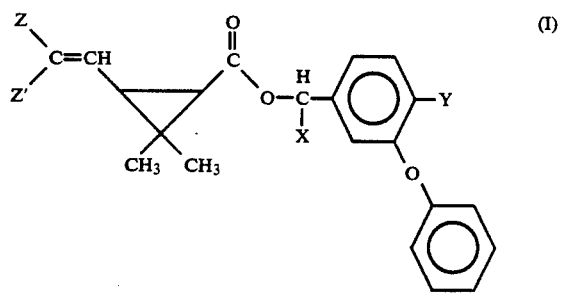

wherein:

Z and Z' are the same or different and each is halo, halo-phenyl or haloalkyl;

X is hydrogen or a cyano group; and Y is hydrogen or a fluorine atom.

Structural formula (I) is intended to encompass all the geometric and optical isomers. More particularly the acid moiety of the ester may be selected from the (+)-cis-isomer, the (+)-trans-isomer, the (±)-cis-isomer, the (±)-trans-isomer and the (±)-cis, trans-isomer, the stereochemistry referring to that of the cyclopropane ring. Moreover, when X is cyano the alcohol moiety of the ester may be selected from the (+)-isomer, the (−)-isomer or the (±)-isomer.

Particularly useful esters are those wherein Z and $Z^1$ are both selected from chloro and bromo. The preferred pyrethroids of this invention are: 3-phenoxybenzyl-(±)-cis,trans-2,2-dimethyl-3-(2,2-dichlorovinyl)cyclopropane-1-carboxylate (permethrin),(−)-α-cyano-3-phenoxybenzyl-(+)-cis-2,2-dimethyl-3-(2,2-dibromovinyl) cycloproprane-1-carboxylate (deltametrin), and (S)-α-cyano-3-phenobenzyl-(1R, 3R)-3-(2,2-dichlorovinyl)-2,2-dimethylcyclopropane-1-carboxylate (alphamethrin, 'FASTAC'), and α-cyano-3-phenoxybenzyl-2,2-dimethyl-3-(2-Permethrin is particularly preferred.

Conveniently, the ratio of permethrin to creosote is within the range 0.001:99.999 to 99.99:0.01. Preferably the said ratio is between 0.1:99.99 and 5.0:95.0, most preferably between 0.1:99.90 and 0.5:99.50. Corresponding ratios of other compounds of Formula I may be derived by comparing their insecticidal potencies with that of permethrin.

Other insecticides, fungicides, preservatives, dyes, solvents and diluents may be added as desired, in which case the overall content of the pyrethroid is preferably about 0.01% to 1%, conveniently 0.1% to 0.5%. A composition in accordance with the invention may be applied to timber to be protected by simply painting the composition onto the timber, or the timber may be sprayed or dipped into a bath of the composition. It is particularly preferred for the composition to be applied to the timber under high pressure.

Instances where it is desirable to protect timber from attack by pests will be well known to the man skilled in the art, but particularly important applications include stakes or poles which are to be sunk partially or wholly into the ground (e.g. fence posts and telegraph posts).

Compositions in accordance with the invention have been found to offer three main advantages. Firstly, the presence of the compound of formula (I) enables the quantity of creosote applied to the timber to be reduced. The treated timber is therefore less oily and smelly, more pleasant to handle and less likely to bleed creosote in a way which may represent a fire hazard. Secondly, it has been found that the creosote stabilises the compound of the formula (I), particularly when the treated timber is buried partially or wholly in the ground, thereby prolonging the period of effective protection afforded by the compound of formula (I). Thirdly, whereas known methods have necessitated two successive treatments, for example CCA and then creosote, which is time-consuming and expensive, the present invention enables a single treatment step to be employed to provide effective protection against ground pests.

It has been found that effective protection can be given to timber by treatment with a composition in accordance with the invention against the following arthropod and fungal pests: wood-boring beetles such as pinhole borers (e.g. Platypus spp., *Diapus quinquespinatus, Xyleborus* spp., and *Ips sexdentatus*), shothole borers (e.g. *Xylothrips religiosae* and *Heterobostrychus aequalis*), powder post beetles (e.g. Minthea spp and *Lyctus brunneus*), wood worm (e.g. *Anobium punctatum*) and longhorn beetles (e.g. *Arhopalus ferus, A. rusticus* and *Hylotrupes bajulus*); termites (e.g. *Cryptotermes cyanocephalus*); staining fungi; moulds; and white, brown and soft rot fungi.

The invention will now be illustrated by way of example.

DETAILED DESCRIPTION OF PREFERRED EMBODIMENTS

EXAMPLE 1

Blocks of Scots pine wood (*Pinus silvestris*) were treated, one side only, with a 0.5% w/w solution of permethrin in white spirit or with a 0.5% w/w solution of permethrin in creosote (British Standard BS144) to give a surface loading to about 200 g of solution per square meter of wood. The blocks were then buried in the ground and shavings were taken at 1, 3, 6 and 9 months after the initial burial, the permethrin in the shavings being extracted into methanol and analysed by g.l.c. The averaged results, in micrograms, are given in Table 1.

TABLE 1

|  | Initial | 1 month | 3 months | 6 months | 9 months |
|---|---|---|---|---|---|
| Permethrin + creosote | 428 | 419 | 419 | 460 | 449 |
| permethrin alone | 382 | 289 | 179 | 170 | 152 |

It can be seen that a considerable amount of permethrin is lost when it is used alone, but not when creosote is present, the apparent increase in the latter being caused by variations in the initial loading across the surface of the block.

EXAMPLE 2

Example 1 was repeated, using cypermethrin or deltametrin instead of permethrin and analysing the blocks after 3 months. The results are given in Table 2:

TABLE 2

|  | Average μg pyrethroid per sample | |
|---|---|---|
|  | Initial | after 3 months |
| Cypermethrin plus creosote (0.25%) | 194 | 201 |
| Cypermethrin (0.25%) | 199 | 140 |
| Deltamethrin (0.05%) plus creosote | 40 | 48 |
| Deltamethrin (0.05%) | 40 | 33 |

EXAMPLE 3

Stability data

To demonstrate that, as stated above, many combinations of pyrethroids and biocidal agents such as fungicides are unstable when mixed, mixtures of permethrin, deltamethrin, tributyl tin oxide (TBTO), tributyl tin phosphate (TBTP), tributyl tin benzoate (TBTB) and copper naphthenate (CuNap) (all known fungicides) were made up in oil solution stored at room temperature, 35° C. or 50° C. and analysed for chemical content after a period of time. The following results were obtained:

TABLE 3A

| Insecticide (% w/w) | Fungicide (% w/w) | Storage Period | Result |
|---|---|---|---|
| Permethrin 0.1% | TBTO 1% | 3 months | unstable at the higher temperatures |
| Permethrin 0.1% | TBTP 1.5% | 12 months | stable |
| Deltamethrin 0.02% | TBTO 1.5% | 2 weeks | unstable |
| Deltamethrin 0.02% | TBTB 1.0% | 12 months | 15% loss of pyrethroid at higher temperatures |
| Deltamethrin 0.01% | CuNap 3.0% | 6 months | unstable |

For comparison, a composition in accordance with the invention yielded the following stability data (Table 3B):

TABLE 3B

|  | Initial | 1 Month | 3 Months | 6 Months |
|---|---|---|---|---|
| Permethrin (0.129%) in creosote (ambient temperature) | 0.129 | 0.129 | 0.122 | 0.126 |
| Permethrin (0.129%) in creosote (50° C.) | 0.129 | 0.129 | 0.125 | 0.123 |

What we claim is:

1. A composition for the treatment of timber comprising permethrin and creosote, the ratio of permethrin to creosote is between 0.001:99.999 to 99.99:0.01.

2. A method of protecting timber, which comprises applying the composition of claim 1 to said timber.

3. A composition for the treatment of timber comprising permethrin and creosote, the ratio of permethrin to creosote is between 0.1:99.90 and 5.0:95.00.

4. Timber in a form for construction having thereon a composition comprising permethrin and creosote, the ratio of permethrin to creosote is between 0.001:99.999 to 99.99:0.01.

5. The timber of claim 4 in the form of a stake or pole.

6. Timber in a form for construction having thereon a composition comprising creosote and a compound of formula I:

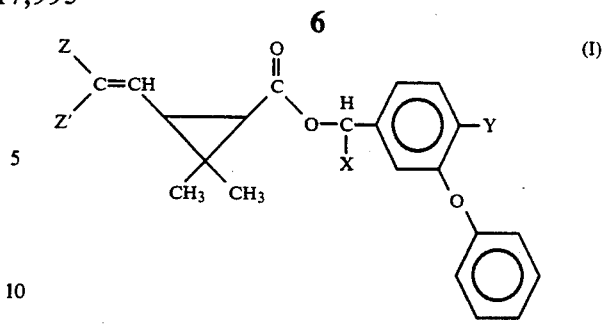
wherein Z and $Z^1$ are the same or different and each is selected from halo, halophenyl and haloalkyl, X is selected from hydrogen and a cyano group and Y is selected from hydrogen and a fluorine atom, the ratio of the compound of formula I to creosote is between 0.001:99.999 to 99.99:0.01.
7. The timber of claim 6 in the form of a stake or pole.
* * * * *